(12) United States Patent
Popplewell et al.

(10) Patent No.: US 7,294,612 B2
(45) Date of Patent: *Nov. 13, 2007

(54) ENCAPSULATED FRAGRANCE CHEMICALS

(75) Inventors: Lewis Michael Popplewell, Morganville, NJ (US); Kaiping Daniel Lee, Morganville, NJ (US); Johan Gerwin Lodewijk Pluyter, Middletown, NJ (US); Joseph Brain, Bussum (NL); Yueqian Zhen, Paoli, PA (US)

(73) Assignee: International Flavors & Fragrances Inc., NY, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/423,467

(22) Filed: Jun. 12, 2006

(65) Prior Publication Data

US 2006/0287205 A1 Dec. 21, 2006

Related U.S. Application Data

(60) Division of application No. 10/720,574, filed on Nov. 24, 2003, now Pat. No. 7,119,057, which is a continuation-in-part of application No. 10/460,610, filed on Jun. 12, 2003, which is a continuation-in-part of application No. 10/268,566, filed on Oct. 10, 2002.

(51) Int. Cl.
*A61K 8/00* (2006.01)
(52) U.S. Cl. .......................... 512/4; 510/119
(58) Field of Classification Search ............ 512/4; 510/119
See application file for complete search history.

(56) References Cited

U.S. PATENT DOCUMENTS

| | | | |
|---|---|---|---|
| 3,599,859 A | 8/1971 | Maierson | |
| 4,234,627 A | 11/1980 | Schilling | |
| 4,386,000 A | 5/1983 | Turner et al. | |
| 4,409,201 A | 10/1983 | Heinrich et al. | |
| 4,746,455 A | 5/1988 | Matsuda et al. | |
| 5,188,753 A | 2/1993 | Schmidt et al. | |
| 6,024,943 A | 2/2000 | Ness et al. | |
| 6,277,404 B1 | 8/2001 | Laversanne et al. | |
| 6,297,203 B1 | 10/2001 | Guskey et al. | |
| 6,329,057 B1 * | 12/2001 | Dungworth et al. | 428/403 |
| 6,730,635 B2 | 5/2004 | Wolf et al. | |
| 6,740,631 B2 * | 5/2004 | Shefer et al. | 510/441 |
| 6,740,713 B1 | 5/2004 | Busch et al. | |
| 6,908,490 B2 | 6/2005 | Boeckh et al. | |
| 7,119,057 B2 * | 10/2006 | Popplewell et al. | 510/438 |
| 7,122,512 B2 * | 10/2006 | Brain et al. | 512/4 |
| 7,125,835 B2 * | 10/2006 | Bennett et al. | 512/4 |
| 2003/0092600 A1 | 5/2003 | Shepherd, Jr. | |
| 2003/0158072 A1 | 8/2003 | Goodson et al. | |

FOREIGN PATENT DOCUMENTS

| | | |
|---|---|---|
| EP | 0376385 | 7/1990 |
| GB | 1561389 | 2/1980 |
| WO | WO 0140430 | 6/2001 |

* cited by examiner

*Primary Examiner*—John R. Hardee
(74) *Attorney, Agent, or Firm*—Elizabeth M. Quiek; Joseph F. Leightner

(57) ABSTRACT

A polymeric encapsulated fragrance is disclosed which is suitable for use in personal care and cleaning products. In a preferred embodiment of the invention the fragrance is encapsulated by a first polymer material to form a fragrance encapsulated polymer, the polymer encapsulated shell is then coated with a cationic polymer, preferably a cationic starch and guar.

6 Claims, No Drawings

ENCAPSULATED FRAGRANCE CHEMICALS

RELATED APPLICATIONS

This application is a divisional of U.S. patent application Ser. No. 10/720,574, filed Nov. 24, 2003, now U.S. Pat. No. 7,119,057; which is a continuation-in-part of U.S. patent application Ser. No. 10/460,610, filed Jun. 12, 2003, now pending; which is a continuation-in-part of U.S. application Ser. No. 10/268,566, filed Oct. 10, 2002, now pending.

FIELD OF THE INVENTION

The present invention relates to fragrance materials that are encapsulated with a polymeric material, the encapsulated fragrance materials are further coated with a cationic polymer material. The encapsulated fragrance materials are well suited for rinse-off applications associated with personal care and cleaning products.

BACKGROUND OF THE INVENTION

Fragrance chemicals are used in numerous products to enhance the consumer's enjoyment of a product. Fragrance chemicals are added to consumer products such as laundry detergents, fabric softeners, soaps, detergents, personal care products, such as shampoos, body washes, deodorants and the like, as well as numerous other products.

In order to enhance the effectiveness of the fragrance materials for the user, various technologies have been employed to enhance the delivery of the fragrance materials at the desired time. One widely used technology is encapsulation of the fragrance material in a protective coating. Frequently the protective coating is a polymeric material. The polymeric material is used to protect the fragrance material from evaporation, reaction, oxidation or otherwise dissipating prior to use. A brief overview of polymeric encapsulated fragrance materials is disclosed in the following U.S. patents: U.S. Pat. No. 4,081,384 discloses a softener or anti-stat core coated by a polycondensate suitable for use in a fabric conditioner; U.S. Pat. No. 5,112,688 discloses selected fragrance materials having the proper volatility to be coated by coacervation with micro particles in a wall that can be activated for use in fabric conditioning; U.S. Pat. No. 5,145,842 discloses a solid core of a fatty alcohol, ester, or other solid plus a fragrance coated by an aminoplast shell; and U.S. Pat. No. 6,248,703 discloses various agents including fragrance in an aminoplast shell that is included in an extruded bar soap.

While encapsulation of fragrance in a polymeric shell can help prevent fragrance degradation and loss, it is often not sufficient to significantly improve fragrance performance in consumer products. Therefore, methods of aiding the deposition of encapsulated fragrances have been disclosed. U.S. Pat. No. 4,234,627 discloses a liquid fragrance coated with an aminoplast shell further coated by a water insoluble meltable cationic coating in order to improve the deposition of capsules from fabric conditioners. U.S. Pat. No. 6,194,375 discloses the use of hydrolyzed polyvinyl alcohol to aid deposition of fragrance-polymer particles from wash products. U.S. Pat. No. 6,329,057 discloses use of materials having free hydroxy groups or pendant cationic groups to aid in the deposition of fragranced solid particles from consumer products.

Despite these and many other disclosures there is an ongoing need for the improved delivery of fragrance materials for various rinse-off products that provide improved performance.

SUMMARY OF THE INVENTION

The present invention is directed to a polymer encapsulated fragrance, the polymer encapsulated fragrance being further treated with a cationic polymer to improve deposition.

More specifically the present invention is directed to a composition comprising:

A fragrance material; said fragrance material encapsulated by a polymer to create a polymer encapsulated fragrance; the polymer encapsulated fragrance being further coated by a cationic polymer. In a preferred embodiment of the invention the cationic polymer is selected from the group consisting of cationic starch and cationic guar. A method for making the cationic coated polymer encapsulated fragrances is also disclosed.

The present invention is well suited for use in rinse off products, which are products that are applied to a substrate and then removed in some manner. Especially preferred products that use the cationic coated polymer encapsulated fragrance of the present invention include, without limitation, hair and pet shampoos, hair conditioners, laundry detergents, fabric conditioners and the like. These and other embodiments of the present invention will become apparent upon referring to the following figure and description of the invention.

DETAILED DESCRIPTION OF THE INVENTION

The fragrances suitable for use in this invention include without limitation, any combination of fragrance, essential oil, plant extract or mixture thereof that is compatible with, and capable of being encapsulated by, a polymer.

Many types of fragrances can be employed in the present invention, the only limitation being the compatibility and ability to be encapsulated by the polymer being employed, and compatability with the encapsulation process used. Suitable fragrances include but are not limited to fruits such as almond, apple, cherry, grape, pear, pineapple, orange, strawberry, raspberry; musk, flower scents such as lavender-like, rose-like, iris-like, and carnation-like. Other pleasant scents include herbal scents such as rosemary, thyme, and sage; and woodland scents derived from pine, spruce and other forest smells. Fragrances may also be derived from various oils, such as essential oils, or from plant materials such as peppermint, spearmint and the like. Other familiar and popular smells can also be employed such as baby powder, popcorn, pizza, cotton candy and the like in the present invention.

A list of suitable fragrances is provided in U.S. Pat. Nos. 4,534,891, 5,112,688 and 5,145,842. Another source of suitable fragrances is found in *Perfumes Cosmetics and Soaps*, Second Edition, edited by W. A. Poucher, 1959. Among the fragrances provided in this treatise are acacia, cassie, chypre, cylamen, fern, gardenia, hawthorn, heliotrope, honeysuckle, hyacinth, jasmine, lilac, lily, magnolia, mimosa, narcissus, freshly-cut hay, orange blossom, orchids, reseda, sweet pea, trefle, tuberose, vanilla, violet, wallflower, and the like.

As used herein olfactory effective amount is understood to mean the amount of compound in perfume compositions the individual component will contribute to its particular olfactory characteristics, but the olfactory effect of the fragrance composition will be the sum of the effects of each of the fragrance ingredients. Thus the compounds of the invention can be used to alter the aroma characteristics of the perfume composition by modifying the olfactory reaction contributed by another ingredient in the composition. The amount will vary depending on many factors including other ingredients, their relative amounts and the effect that is desired.

The level of fragrance in the cationic polymer coated encapsulated fragrance varies from about 5 to about 95 weight percent, preferably from about 40 to about 95 and most preferably from about 50 to about 90 weight percent on a dry basis. In addition to the fragrance other agents can be used in conjunction with the fragrance and are understood to be included.

As noted above, the fragrance may also be combined with a variety of solvents which serve to increase the compatibility of the various materials, increase the overall hydrophobicity of the blend, influence the vapor pressure of the materials, or serve to structure the blend. Solvents performing these functions are well known in the art and include mineral oils, triglyceride oils, silicone oils, fats, waxes, fatty alcohols, diisodecyl adipate, and diethyl phthalate among others.

A common feature of many encapsulation processes is that they require the fragrance material to be encapsulated to be dispersed in aqueous solutions of polymers, pre-condensates, surfactants, and the like prior to formation of the capsule walls. Therefore, materials having low solubility in water, such as highly hydrophobic materials are preferred, as they will tend to remain in the dispersed perfume phase and partition only slightly into the aqueous solution. Fragrance materials with Clog P values greater than 1, preferably greater than 3, and most preferably greater than 5 will thus result in micro-capsules that contain cores most similar to the original composition, and will have less possibility of reacting with materials that form the capsule shell.

One object of the present invention is to deposit capsules containing fragrance cores on desired substrates such as cloth, hair, and skin during washing and rinsing processes. Further, it is desired that, once deposited, the capsules release the encapsulated fragrance either by diffusion through the capsule wall, via small cracks or imperfections in the capsule wall caused by drying, physical, or mechanical means, or by large-scale rupture of the capsule wall. In each of these cases, the volatility of the encapsulated perfume materials is critical to both the speed and duration of release, which in turn control consumer perception. Thus, fragrance chemicals which have higher volatility as evidenced by normal boiling points of less than 250° C., preferably less than about 225° C. are preferred in cases where quick release and impact of fragrance is desired. Conversely, fragrance chemicals that have lower volatility (boiling points greater than 225° C.) are preferred when a longer duration of aroma is desired. Of course, fragrance chemicals having varying volatility may be combined in any proportions to achieve the desired speed and duration of perception.

In order to provide the highest fragrance impact from the fragrance encapsulated capsules deposited on the various substrates referenced above, it is preferred that materials with a high odor-activity be used. Materials with high odor-activity can be detected by sensory receptors at low concentrations in air, thus providing high fragrance perception from low levels of deposited capsules. This property must be balanced with the volatility as described above. Some of the principles mentioned above are disclosed in U.S. Pat. No. 5,112,688.

Further, it is clear that materials other than fragrances may be employed in the system described here. Examples of other materials which may be usefully deposited from rinse-off products using the invention include sunscreens, softening agents, insect repellents, and fabric conditioners, among others.

Encapsulation of fragrances is known in the art, see for example U.S. Pat. Nos. 2,800,457, 3,870,542, 3,516,941, 3,415,758, 3,041,288, 5,112,688, 6,329,057, and 6,261,483. Another discussion of fragrance encapsulation is found in the Kirk-Othmer Encyclopedia.

Preferred encapsulating polymers include those formed from melamine-formaldehyde or urea-formaldehyde condensates, as well as similar types of aminoplasts. Additionally, capsules made via the simple or complex coacervation of gelatin are also preferred for use with the coating. Capsules having shell walls comprised of polyurethane, polyamide, polyolefin, polysaccaharide, protein, silicone, lipid, modified cellulose, gums, polyacrylate, polyphosphazines, polystyrene, and polyesters or combinations of these materials are also functional.

A representative process used for aminoplast encapsulation is disclosed in U.S. Pat. No. 3,516,941 though it is recognized that many variations with regard to materials and process steps are possible. A representative process used for gelatin encapsulation is disclosed in U.S. Pat. No. 2,800,457 though it is recognized that many variations with regard to materials and process steps are possible. Both of these processes are discussed in the context of fragrance encapsulation for use in consumer products in U.S. Pat. Nos. 4,145,184 and 5,112,688 respectively.

Well known materials such as solvents, surfactants, emulsifiers, and the like can be used in addition to the polymers described above to encapsulate the fragrance without departing from the scope of the present invention. It is understood that the term encapsulated is meant to mean that the fragrance material is substantially covered in its entirety. Encapsulation can provide pore vacancies or interstitial openings depending on the encapsulation techniques employed. More preferably the entire fragrance material portion of the present invention is encapsulated.

Particles comprised of fragrance and a variety of polymeric and non-polymeric matrixing materials are also suitable for use. These may be composed of polymers such as polyethylene, fats, waxes, or a variety of other suitable materials. Essentially any capsule, particle, or dispersed droplet may be used that is reasonably stable in the application and release of fragrance at an appropriate time once deposited.

Particle and capsule diameter can vary from about 10 nanometers to about 1000 microns, preferably from about 50 nanometers to about 100 microns and is most preferably from about 2 to about 15 microns. The capsule distribution can be narrow, broad, or multi-modal. Each modal of the multi-modal distributions may be composed of a different type of capsule chemistry.

Once the fragrance material is encapsulated a cationically charged water-soluble polymer is applied to the fragrance encapsulated polymer. This water-soluble polymer can also be an amphoteric polymer with a ratio of cationic and anionic functionalities resulting in a net total charge of zero and positive, i.e., cationic. Those skilled in the art would appreciate that the charge of these polymers can be adjusted by changing the pH, depending on the product in which this technology is to be used. Any suitable method for coating the cationically charged materials onto the encapsulated fragrance materials can be used. The nature of suitable cationically charged polymers for assisted capsule delivery to interfaces depends on the compatibility with the capsule wall chemistry since there has to be some association to the capsule wall. This association can be through physical interactions, such as hydrogen bonding, ionic interactions, hydrophobic interactions, electron transfer interactions or, alternatively, the polymer coating could be chemically (covalently) grafted to the capsule or particle surface. Chemical modification of the capsule or particle surface is another way to optimize anchoring of the polymer coating to capsule or particle surface. Furthermore, the capsule and the polymer need to want to go to the desired interface and, therefore, need to be compatible with the chemistry (polarity, for instance) of that interface. Therefore, depending on which capsule chemistry and interface (e.g., cotton, polyester, hair, skin, wool) is used the cationic polymer can be selected from one or more polymers with an overall zero (amphoteric: mixture of cationic and anionic functional groups) or net positive charge, based on the following polymer backbones: polysaccharides, polypeptides, polycarbonates, polyesters, polyolefinic (vinyl, acrylic, acrylamide, poly diene), polyester, polyether, polyurethane, polyoxazoline, polyamine, silicone, polyphosphazine, olyaromatic, poly heterocyclic, or polyionene, with molecular weight (MW) ranging from about 1,000 to about 1000,000,000, preferably from about 5,000 to about 10,000,000. As used herein molecular weight is provided as weight average molecular weight. Optionally, these cationic polymers can be used in combination with nonionic and anionic polymers and surfactants, possibly through coacervate formation.

A more detailed list of cationic polymers that can be used to coat the encapsulated fragrance is provided below:

Polysaccharides include but are not limited to guar, alginates, starch, xanthan, chitosan, cellulose, dextrans, arabic gum, carrageenan, hyaluronates. These polysaccharides can be employed with:

(a) cationic modification and alkoxy-cationic modifications, such as cationic hydroxyethyl, cationic hydroxy propyl. For example, cationic reagents of choice are 3-chloro-2-hydroxypropyl trimethylammonium chloride or its epoxy version. Another example is graftcopolymers of polyDADMAC on cellulose like in Celquat L-200 (Polyquaternium-4), Polyquaternium-10 and Polyquaternium-24, commercially available from National Starch, Bridgewater, N.J.;

(b) aldehyde, carboxyl, succinate, acetate, alkyl, amide, sulfonate, ethoxy, propoxy, butoxy, and combinations of these functionalities. Any combination of Amylose and Amylopectin and overall molecular weight of the polysaccharide; and (c) any hydrophobic modification (compared to the polarity of the polysaccharide backbone).

The above modifications described in (a), (b) and (c) can be in any ratio and the degree of functionalization up to complete substitution of all functionalizable groups, and as long as the theoretical net charge of the polymer is zero (mixture of cationic and anionic functional groups) or preferably positive. Furthermore, up to 5 different types of functional groups may be attached to the polysaccharides. Also, polymer graft chains may be differently modified than the backbone. The counterions can be any halide ion or organic counter ion. U.S. Pat. No. 6,297,203 and U.S. Pat. No. 6,200,554.

Another source of cationic polymers contain protonatable amine groups so that the overall net charge is zero (amphoteric: mixture of cationic and anionic functional groups) or positive. The pH during use will determine the overall net charge of the polymer. Examples are silk protein, zein, gelatin, keratin, collagen and any polypeptide, such as polylysine.

Further cationic polymers include poly vinyl polymers, with up to 5 different types of monomers, having the monomer generic formula —C(R2)(R1)-CR2R3-. Any co-monomer from the types listed in this specification may also be used. The overall polymer will have a net theoretical positive charge or equal to zero (mixture of cationic and anionic functional groups). Where R1 is any alkanes from C1-C25 or H; the number of double bonds ranges from 0-5. Furthermore, R1 can be an alkoxylated fatty alcohol with any alkoxy carbon-length, number of alkoxy groups and C1-C25 alkyl chain length. R1 can also be a liquid crystalline moiety that can render the polymer thermotropic liquid crystalline properties, or the alkanes selected can result in side-chain melting. In the above formula R2 is H or CH3; and R3 is —Cl, —NH2 (i.e., poly vinyl amine or its copolymers with N-vinyl formamide. These are sold under the name Lupamin 9095 by BASF Corporation), —NHR1, —NR1R2, —NR1R2 R6 (where R6=R1, R2, or —CH2-COOH or its salt), —NH—C(O)—H, —C(O)—NH2 (amide), —C(O)—N(R2)(R2')(R2''), —OH, styrene sulfonate, pyridine, pyridine-N-oxide, quaternized pyridine, imidazolinium halide, imidazolium halide, imidazol, piperidine, pyrrolidone, alkyl-substituted pyrrolidone, caprolactam or pyridine, phenyl-R4 or naphthalene-R5 where R4 and R5 are R1, R2, R3, sulfonic acid or its alkali salt —COOH, —COO— alkali salt, ethoxy sulphate or any other organic counter ion. Any mixture or these R3 groups may be used. Further suitable cationic polymers containing hydroxy alkyl vinyl amine units, as disclosed in U.S. Pat. No. 6,057,404.

Another class of materials are polyacrylates, with up to 5 different types of monomers, having the monomer generic formula: —CH(R1)—C(R2)(CO—R3—R4)-. Any co-monomer from the types listed in this specification may also be used. The overall polymer will have a net theoretical positive charge or equal to zero (mixture of cationic and anionic functional groups). In the above formula R1 is any alkane from C1-C25 or H with number of double bonds from 0-5, aromatic moieties, polysiloxane, or mixtures thereof. Furthermore, R1 can be an alkoxylated fatty alcohol with any alkoxy carbon-length, number of alkoxy groups and C1-C25 alkyl chain length. R1 can also be a liquid crystalline moiety that can render the polymer thermotropic liquid crystalline properties, or the alkanes selected can result in side-chain melting. R2 is H or CH3; R3 is alkyl alcohol C1-25 or an alkylene oxide with any number of double bonds, or R3 may be absent such that the C=O bond is (via the C-atom) directly connected to R4. R4 can be: —NH2, NHR1, —NR1R2, —NR1R2 R6 (where R6=R1, R2, or —CH2-COOH or its salt), —NH—C(O)—, sulfo betaine, betaine, polyethylene oxide, poly(ethyleneoxide/propylene oxide/butylene oxide) grafts with any end group, H, OH, styrene sulfonate, pyridine, quaternized pyridine, alkyl-substituted pyrrolidone or pyridine, pyridine-N-oxide, imidazolinium halide, imidazolium halide, imidazol, piperidine, —OR1, —OH, —COOH alkali salt, sulfonate, ethoxy sulphate, pyrrolidone, caprolactam, phenyl-R4 or naphthalene-R5 where R4 and R5 are R1, R2, R3, sulfonic acid or its alkali salt or organic counter ion. Any mixture or these R3 groups may be used. Also, glyoxylated cationic polyacrylamides can be used. Typical polymers of choice are those containing the cationic monomer dimethylaminoethyl methacrylate (DMAEMA) or methacrylamidopropyl trimethyl ammonium chloride (MAPTAC). DMAEMA can be found in Gafquat and Gaffix VC-713 polymers from ISP. MAPTAC can be found in BASF's Luviquat PQ11 PN and ISP's Gafquat HS100.

Another group of polymers that can be used are those that contain cationic groups in the main chain or backbone. Included in this group are:

(1) polyalkylene imines such as polyethylene imine, commercially available as Lupasol from BASF. Any molecular weight and any degree of crosslinking of this polymer can be used in the present invention;

(2) ionenes having the general formula set forth as —[N(+)R1R2-A1-N(R5)-X—N(R6)-A2-N(+)R3R4-A3]n-2Z-, as disclosed in U.S. Pat. No. 4,395,541 and U.S. Pat. No. 4,597,962;

(3) adipic acid/dimethyl amino hydroxypropyl diethylene triamine copolymers, such as Cartaretin F-4 and F-23, commercially available from Sandoz;

(4) polymers of the general formula —[N(CH3)2-(CH2)x-NH—(CO)—NH—(CH2)y-N(CH3)2)-(CH2)z-O—(CH2)p]n-, with x, y, z, p=1-12, and n according to the molecular weight requirements. Examples are Polyquaternium 2 (Mirapol A-15), Polyquaternium-17 (Mirapol AD-1), and Polyquaternium-18 (Mirapol AZ-1).

Other polymers include cationic polysiloxanes and cationic polysiloxanes with carbon-based grafts with a net theoretical positive charge or equal to zero (mixture of cationic and anionic functional groups). This includes cationic end-group functionalized silicones (i.e. Polyquaternium-80). Silicones with general structure: -[—Si(R1)(R2)-O-]x-[Si(R3)(R2)-O-]y- where R1 is any alkane from C1-C25 or H with number of double bonds from 0-5, aromatic moieties, polysiloxane grafts, or mixtures thereof. R1 can also be a liquid crystalline moiety that can render the polymer thermotropic liquid crystalline properties, or the alkanes selected can result in side-chain melting. R2 can be H or CH3 and R3 can be —R1-R4, where R4 can be —NH2, —NHR1, —NR1R2, —NR1R2R6 (where R6=R1, R2, or —CH2-COOH or its salt), —NH—C(O)—, —COOH, —COO— alkali salt, any C1-25 alcohol, —C(O)—NH2 (amide), —C(O)—N(R2)(R2')(R2"), sulfo betaine, betaine, polyethylene oxide, poly(ethyleneoxide/propylene oxide/butylene oxide) grafts with any end group, H, —OH, styrene sulfonate, pyridine, quaternized pyridine, alkyl-substituted pyrrolidone or pyridine, pyridine-N-oxide, imidazolinium halide, imidazolium halide, imidazol, piperidine, pyrrolidone, caprolactam, —COOH, —COO— alkali salt, sulfonate, ethoxy sulphate phenyl-R5 or naphthalene-R6 where R5 and R6 are R1, R2, R3, sulfonic acid or its alkali salt or organic counter ion. R3 can also be —(CH2)x-O—CH2-CH(OH)—CH2-N(CH3)2-CH2-COOH and its salts. Any mixture of these R3 groups can be selected. X and y can be varied as long as the theoretical net charge of the polymer is zero (amphoteric) or positive. In addition, polysiloxanes containing up to 5 different types of monomeric units may be used. Examples of suitable polysiloxanes are found in U.S. Pat. Nos. 4,395,541 4,597,962 and U.S. Pat. No. 6,200,554. Another group of polymers that can be used to improve capsule/particle deposition are phospholipids that are modified with cationic polysiloxanes. Examples of these polymers are found in U.S. Pat. No. 5,849,313, WO Patent Application 9518096A1 and European Patent EP0737183B1.

Furthermore, copolymers of silicones and polysaccharides and proteins can be used (Crodasone Series).

Another class of polymers include polyethylene oxide-co-propyleneoxide-co-butylene oxide polymers of any ethylene oxide/propylene oxide/butylene oxide ratio with cationic groups resulting in a net theoretical positive charge or equal to zero (amphoteric). The general structure is:

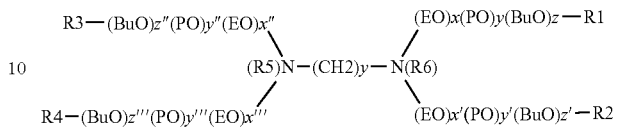

where R1,2,3,4 is —NH2, —N(R)3-X+, R with R being H or any alkyl group. R5,6 is —CH3 or H. Counter ions can be any halide ion or organic counter ion. X, Y, may be any integer, any distribution with an average and a standard deviation and all 12 can be different. Examples of such polymers are the commercially available TETRONIC brand polymers.

Suitable polyheterocyclic (the different molecules appearing in the backbone) polymers include the piperazine-alkylene main chain copolymers disclosed in *Ind. Eng. Chem. Fundam.*, (1986), 25, pp. 120-125, by Isamu Kashiki and Akira Suzuki.

Also suitable for use in the present invention are copolymers containing monomers with cationic charge in the primary polymer chain. Up to 5 different types of monomers may be used. Any co-monomer from the types listed in this specification may also be used. Examples of such polymers are poly diallyl dimethyl ammonium halides (PolyDADMAC) copolymers of DADMAC with vinyl pyrrolidone, acrylamides, imidazoles, imidazolinium halides, etc. These polymers are disclosed in Henkel EP0327927A2 and PCT Patent Application 01/62376A1. Also suitable are Polyquaternium-6 (Merquat 100), Polyquaternium-7 (Merquats S, 550, and 2200), Polyquaternium-22 (Merquats 280 and 295) and Polyquaternium-39 (Merquat Plus 3330), available from Ondeo Nalco.

Polymers containing non-nitrogen cationic monomers of the general type —CH2-C(R1)(R2-R3-R4)- can be used with: R1 being a —H or C1-C20 hydrocarbon. R2 is a disubstituted benzene ring or an ester, ether, or amide linkage. R3 is a C1-C20 hydrocarbon, preferably C1-C10, more preferably C1-C4. R4 can be a trialkyl phosphonium, dialkyl sulfonium, or a benzopyrilium group, each with a halide counter ion. Alkyl groups for R4 are C1-C20 hydrocarbon, most preferably methyl and t-butyl. These monomers can be copolymerized with up to 5 different types of monomers. Any co-monomer from the types listed in this specification may also be used.

Substantivity of these polymers may be further improved through formulation with cationic, amphoteric and nonionic surfactants and emulsifiers, or by coacervate formation between surfactants and polymers or between different polymers. Combinations of polymeric systems (including those mentioned previously) may be used for this purpose as well as those disclosed in EP1995/000400185.

Furthermore, polymerization of the monomers listed above into a block, graft or star (with various arms) polymers can often increase the substantivity toward various surfaces. The monomers in the various blocks, graft and arms can be selected from the various polymer classes listed in this specification and the sources below:

Encyclopedia of Polymers and Thickeners for Cosmetics, Robert Lochhead and William From, in Cosmetics & Toiletries, Vol. 108, May 1993, pp. 95-138;

Modified Starches: Properties & Uses, O. B. Wurzburg, CRC Press, 1986. Specifically, Chapters 3, 8, and 10; U.S. Pat. Nos. 6,190,678 and 6,200,554; and PCT Patent Application WO 01/62376A1 assigned to Henkel.

The preferred cationically charged materials are selected from the group consisting of cationically modified starch and cationically modified guar, polymers comprising poly diallyl dimethyl ammonium halides (PolyDADMAC), and copolymers of DADMAC with vinyl pyrrolidone, acrylamides, imidazoles, imidazolinium halides, and the like. For instance, Polyquaternium-6, 7, 22 and 39, all available from Ondeo Nalco.

The preferred cationic starch has a molecular weight of from about 100,000 to about 500,000,000, preferably from about 200,000 to about 10,000,000 and most preferably from about 250,000 to about 5,000,000. The preferred cationic starch products are HI-CAT CWS42 and HI-CAT 02 and are commercially available from ROQUETTE AMERICA, Inc.

The preferred cationic guar has a molecular weight of from about 50,000 to about 5,000,000. The preferred cationic guar products are Jaguar C-162 and Jaguar C-17 and are commercially available from Rhodia Inc.

The level of cationic polymer is from about 1% to about 3000%, preferably from about 5% to about 1000% and most preferably from about 10% to about 500% of the fragrance containing compositions, based on a ratio with the fragrance on a dry basis.

The weight ratio of the encapsulating polymer to fragrance is from about 1:25 to about 1:1. Preferred products have had the weight ratio of the encapsulating polymer to fragrance varying from about 1:10 to about 4:96.

For example, if a capsule blend has 20 weight % fragrance and 20 weight % polymer, the polymer ratio would be (20/20) multiplied by 100 (%)=100%.

The present invention, the encapsulated fragrance is well suited for wash-off products. Wash-off products are understood to be those products that are applied for a given period of time and then are removed. These products are common in areas such as laundry products, and include detergents, fabric conditioners, and the like; as well as personal care products which include shampoos, hair rinses, body washes, soaps and the like.

As described herein, the present invention is well suited for use in a variety of well-known consumer products such as laundry detergent and fabric softeners, liquid dish detergents, automatic dish detergents, as well as hair shampoos and conditioners. These products employ surfactant and emulsifying systems that are well known. For example, fabric softener systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, 4,767,547, 4,424,134. Liquid dish detergents are described in U.S. Pat. Nos. 6,069,122 and 5,990,065; automatic dish detergent products are described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562. Liquid laundry detergents which can use the present invention include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818. Shampoo and conditioners that can employ the present invention include U.S. Pat. Nos. 6,162,423, 5,968,286, 5,935561, 5,932,203, 5,837,661, 5,776,443, 5,756,436, 5,661,118, 5,618,523, 5,275,755, 5,085,857, 4,673,568, 4,387,090, 4,705,681.

We have discovered that the present invention is advantageously applied to products, including fabric rinse conditioners, having a pH of less than 7, preferably less than about 5 and most preferably less than about 4.

A better product, including wash-off products such as fabric rinse conditioner is also obtained when the salt level is limited. The improvement in the fabric rinse conditioner is noted by a longer lasting and/or improved delivery of fragrance. One method of improving the delivery of the encapsulated fragrance is to limit the amount of salt in the product base. Preferably the level of salt in the rinse conditioner product is less than or equal to about 1 weight percent by weigh in the product, preferably less than about 0.5 weight percent and most preferably less than about 0.1 weight percent.

More specifically we have discovered that limiting the level of calcium chloride will improve the delivery of the fragrance using the encapsulated fragrance of the present invention. Improved fragrance delivery is provided by limiting the amount of calcium chloride to less than about 2 weight percent, typically less than 1 weight percent and more preferably less than 0.5 weight percent. As it is known in the art, calcium chloride is added to control viscosity of the formulations, so there is trade-off between the viscosity and fragrance delivery. We have discovered that limiting the level of calcium chloride level as set forth above is particularly advantageous in fabric rinse conditioner products.

Another means for improving the performance of delivery of the encapsulated fragrance of the present invention is to limit the level of some softening agents. We have discovered that limiting the softening actives, such as triethanolamine quaternary, diethanolamine quaternary, ACCOSOFT cationic surfactants (Stepan Chemical), or ditallow dimethyl ammonium chloride (DTDMAC), to an amount of from about 5 to about 40 weight percent of the product, preferably from about 10 to about 30 and more preferably from about 5 to 15 weight percent of a fabric rinse conditioner product will improve the performance of the fragrance. The above softening agents are well known in the art and are disclosed in U.S. Pat. Nos. 6,521,589 and 6,180,594.

Yet another means for improving fragrance delivery of the present invention is to limit the level of the non-ionic surfactants employed in the product, including a fabric softening product. Many non-ionic surfactants are known in the art and include alkyl ethoxylate, commercially available as NEODOL (Shell Oil Company), nonyl phenol ethoxylate, TWEEN surfactants (ICI Americas Inc.), and the like. We have discovered that the encapsulated fragrance of the present invention are advantageously used when the non-ionic surfactant level is below about 5 weight percent of the product, preferably less than about 1 weight percent and most preferably less than 0.5 weight percent.

Yet another means for enhancing the fabric softener product is to limit the level of co-solvent included in the fabric softener in addition to water. Reducing the level of co solvents such as ethanol and isopropanol to less than about 5 weight percent of the product, preferably less than about 2 and most preferably less than about 1 weight percent of the fabric softener product has been found to improve fragrance delivery.

Improved fragrance performance includes longer lasting fragrance, improved substantivity of the fragrance on cloth or the ability to provide improved fragrance notes, such as specific fragrance notes through the use of the present invention.

While the above description is primarily to fabric rinse conditioner products, additional studies for shampoos, detergent and other cleaning products have also led to preferred embodiments for these products as well.

As was found for fabric rinse conditioners, additional studies have determined that lower pH is desirable for the delivery of fragrance when used in the product base. The preferred bases are neutral or mildly acidic, preferably having a pH of 7, more preferably less than about 5 and most preferably less than about 4 for shampoos, detergent and other cleaning products.

We have found that powder detergent and other cleaning products provide enhanced fragrance delivery when the material coating the encapsulating polymer is also neutral or slightly acidic. Preferred materials are NaHSO4, acetic acid, citric acid and other similar acidic materials and their mixtures. These materials have a pH of less than about 7, preferably less than about 5 and most preferably less than about 4.

As was described with fabric rinse conditioners, lower surfactant levels were advantageously employed in shampoos, detergents and other cleaning products bases with the present invention. The level of surfactant is preferably less than about 30, more preferably less than about 20 and most preferably less than about 10 weight percent of the product base. A similar finding was found with preferred levels of salt in shampoos, detergents and other cleaning products as was found in fabric rinse conditioners. The salt level is preferably less than about 5 weight percent, more preferably less than about 2 and most preferably less than 0.5 weight percent of the product.

Lower solvent levels found in the base improves the fragrance delivery in shampoos, detergents and other cleaning products as well. Solvents, include but are not limited to, ethanol, isopropanol, dipropylene glycol in addition to the water base and the hydrotope level is preferably less than 5 weight percent, preferably less than about 2 and most preferably less than 1 weight percent of the total product base.

A preferred surfactant base for shampoos, detergents and other cleaning products was found to be ethoxylated surfactants such as alkyl ethoxylated sulfates, ($C_{12}$-$C_{14}$)(ethylene oxide)nSO$_4$M; or ethoxylated carboxylate surfactants ($C_{12}$-$C_{14}$)(Ethylene oxide)nCOOM where n is from 1 to about 50 and M is Na$^+$, K$^+$ or NH4$^+$ cation. Other preferred anionic surfactants are alkoyl isthionates such as sodium cocoly isthionate, taurides, alpha olefin sulphonates (i.e., Bioterge, Stepan Corporation), sulfosuccinates, such as Standapol SH-100 (Cognis) and disodium laureth sulfosuccinate (Stepan Mild SL3-BA, Stepan Corporation). A more preferred class of surfactants for use in the present invention was zwitterionic surfactants such as the alkyl amine oxides, amidealkyl hydroxysultaines like amidopropyl hydroxyl sultaine (Amphosol CS-50, Stepan Corporation), amphoacetates, such as sodium cocamphoacetate (Amphosol IC, Stepan Corporation), betaines and sulfobetaines. Zwitterionic surfactants are disclosed in greater detail in U.S. Pat. No. 6,569,826. Other commercially available surfactants are AMPHOSOL series of betaines (Stepan Chemical); TEGO-TIAN by Goldschmidt; and HOSTAPAN and ARKOPAN by Clariant The most preferred surfactant system to be employed with the encapsulated fragrance system of the present invention was found to be non-ionic surfactants. Nonionic surfactants that may be used include the primary and secondary alcohol ethoxylates, especially the $C_8$-$C_{20}$ aliphatic alcohols ethoxylated with an average of from 1 to 50 moles of ethylene oxide per mole of alcohol, and more especially the $C_{10}$-$C_{15}$ primary and secondary aliphatic alcohols ethoxylated with an average of from 1 to 10 moles of ethylene oxide per mole of alcohol. Other ethoxylated nonionic surfactants that are suitable are polyethylene glycol (MW=200-6000) esters of fatty acids, ethylene oxide-propylene oxide-butylene oxide block copolymers such as the Pluronic and Tetronic polymers made by BASF and ethoxylated alkanolamides such as, PEG-6 cocamide (Ninol C-5, Stepan Corporation). Non-ethoxylated nonionic surfactants include alkylpolyglycosides, glycerol monoethers, polyhydroxyamides (glucamide), polyglycerol fatty acid esters, alkyl pyrrolidone-based surfactants (Surfadone LP-100 and LP300, ISP Corporation), dialkyl phthalic acid amides (distearyl phthalic acid amide or Stepan SAB-2 by Stepan Corporation), alkyl alkanolamides, such as Laureth Diethanolamide (Ninol 30-LL, Stepan Corporation). These nonionic surfactants are disclosed in U.S. Pat. No. 6,517,588.

In addition, Gemini surfactants can be used, such as the Gemini polyhydroxy fatty acid amides disclosed in U.S. Pat. No. 5,534,197. Furthermore, structured liquids can be used that contain lamellar vesicles or lamellar droplets, as disclosed in WO 9712022 A, WO 9712027 A1, U.S. Pat. Nos. 5,160,655, and 5,776,883.

Polymers that are known as deposition aids, and in a preferred embodiment are also cationic can be found in the following resources:

The rinse-off products that are advantageously used with the polymer encapsulated fragrance of the present invention include laundry detergents, fabric softeners, bleaches, brighteners, personal care products such as shampoos, rinses, creams, body washes and the like. These may be liquids, solids, pastes, or gels, of any physical form. Also included in the use of the encapsulated fragrance are applications where a second active ingredient is included to provide additional benefits for an application. The additional beneficial ingredients include fabric softening ingredients, skin moisturizers, sunscreen, insect repellent and other ingredients as may be helpful in a given application. Also included are the beneficial agents alone, that is without the fragrance.

While the preferred coating materials may be simply dissolved in water and mixed with a suspension of capsules prior to addition to the final product, other modes of coating use and application are also possible. These modes include drying the coating solution in combination with the capsule suspension for use in dry products such as detergents, or using higher concentrations of coating such that a gel structure is formed, or combining the coating material with other polymers or adjuvants which serve to improve physical characteristics or base compatibility. Drying or reducing the water content of the capsule suspension prior to coating addition is also possible, and may be preferable when using some coating materials. Further, when using some coating materials it is possible to add the coating to the application base separately from the encapsulated fragrance.

Solvents or co-solvents other than water may also be employed with the coating materials. Solvents that can be employed here are (i) polyols, such as ethylene glycol, propylene glycol, glycerol, and the like, (ii) highly polar organic solvents such as pyrrolidine, acetamide, ethylene diamine, piperazine, and the like, (iii) humectants/plasticizers for polar polymers such as monosaccharides (glucose, sucrose, etc.), amino acids, ureas and hydroxyethyl modified ureas, and the like, (iv) plasticizers for less polar polymers, such as diisodecyl adipate (DIDA), phthalate esters, and the like.

Rheology modifiers should be selected carefully to insure compatibility with the deposition agents. Preferred are non-ionic, cationic and amphoteric thickeners, such as modified polysaccharides (starch, guar, celluloses), polyethylene imine (Lupasol WF, BASF Corporation), acrylates (Structure Plus, National Starch and Chemical Company) and cationic silicones.

The coating polymer(s) may also be added to a suspension of capsules that contain reactive components such that the coating becomes chemically (covalently) grafted to the capsule wall, or the coating polymer(s) may be added during the crosslinking stage of the capsule wall such that covalent partial grafting of the coating takes place.

The present invention also includes the incorporation of a silicone or a siloxane material into a product that contains encapsulated fragrances of the present invention. As used herein silicone is meant to include both silicone and siloxane materials. Also included in the definition of silicone materials are the cationic and quaternized of the silicones. These materials are well known in the art and include both linear and branched polymers.

In addition to silicones, the present invention also includes the use of mineral oils, triglyceride oils, polyglycerol fatty acid esters and sucrose polyester materials in a similar matter as the silicone materials. For brevity, these materials are understood to be included in the term silicone as used in this specification unless noted to the contrary. Those with skill in the art will also appreciate that it is possible to incorporate a silicone in combination with mineral oils and the like in carrying out the present invention.

The silicone material is preferably admixed to the encapsulated fragrance-containing product after the fragrance materials are encapsulated. Optionally, the silicone material may be mixed directly with the product base either before or after the encapsulated fragrance has been added.

Suitable silicone materials include amodiemthicone, polymethylalkyl siloxanes, polydimethylalkyl siloxanes, dimethicone, dimethicone copolyol, dimethiconol, disiloxane, cyclohexasiloxane, cyclomethicone, cyclopentasiloxane, phenyl dimethicone, phenyl trimethicone, silicone quaternarary materials including silicone quaternium-8, and silicone quaternium-12, trimethylsiloxyamidodimethicone, trimethylsiloxysilicate and the like. These materials are commercially well known materials and are available from suppliers such as Dow Corning, Shin-Etsu, Wacker Silicones Corporation and the like. The preferred silicon is Dow Corning 245 Fluid (Dow Corning, Midland Mich.), which is described as containing greater than about 60 weight percent decamethylcyclopentasiloxane and less than or equal to about 4 weight percent dimethylcyclosiloxanes.

Amino functional silicone oils such as those described in U.S. Pat. Nos. 6,355,234 and 6,436,383 may also be used in the present invention.

Preferably the silicone materials of the present invention have a molecular weight (Mw) of from about 100 to about 200,000, preferably from about 200 to about 100,00 and most preferably from about 300 to about 50,000.

The viscosity of the silicone materials is typically from 0.5 to about 25, preferably from about 1 to about 15 and most preferably from about 2 to about 10 millimeters$^2$ sec-1 using the Corporate Test Method as described in the Dow Corning product brochures.

The level of silicone used in the present invention varies by product, but is typically less than 10 percent by weight, typically from about 0.5 to about 8 weight percent of the total weight of product. Preferably the silicon level is from about 2 to about 6 and most preferably from about 3 to about 5 weight percent of the total weight of the product.

The silicon fluid can be added to a wide array of products in order to enhance the delivery of fragrance. Suitable products include fabric conditioners and detergents, personal care products such as shampoos, liquid soap, body washes and the like; as well as in applications such as fine fragrances and colognes.

For example, a representative formulation for a fabric softener rinse product would include the following materials:

cationic quaternary ammonium softeners from about 3 to about 30 weight percent;

the encapsulated fragrance product of the present invention from about 0.1 to about 5 weight percent; and a silicone oil form about 1 to about 10 weight percent.

The remainder of the fabric softener product may additionally contain, without limitation, brighteners, dispersibility aids, surfactants, stabilizers, soil release agents and water.

Without wishing to be bound by any theory it is believed that the silicone fluid prevents the encapsulated fragrance material from leaching from the capsule. Although the encapsulation materials are provided to prevent the loss of fragrance before usage, it is believed that the surfactants found in detergents, fabric conditioners, shampoos and other wash-off products over time leach some of the fragrance from the capsule during storage and before use. The addition of the silicone fluids to the fragrance-containing capsule materials is believed to coat the encapsulation materials with a layer of silicone that prevents the leaching of the fragrance. Another rationale for the improvement of the delivery of fragrance by the addition of silicone oils is that the oils fill vesicles in the product base. The product base such as a detergent, contains high levels of surfactant, and it is theorized that the high level of surfactant in the product bases over time removes the fragrance from the capsule. The addition of silicone to the slurry containing the encapsulated fragrance is theorized to slow the leaching of the fragrance by the surfactant, thereby providing additional and longer lasting fragrance to be delivered over time.

In another embodiment of the present invention, we have discovered that the cationic coating is not required and that the inclusion of silicon in the encapsulated mixture can provide satisfactory performance in the delivery of the fragrance. In this embodiment of the invention, the fragrance is encapsulated by the polymeric materials described above, and the level of silicon described above is provided to the encapsulated fragrance.

More specifically the present invention is directed to a composition comprising a fragrance material, said fragrance material encapsulated by a polymer to provide a polymer encapsulated fragrance, said polymer encapsulated fragrance further provided with a silicone material. This embodiment differs from other embodiments of the present invention in that the cationic polymer is not provided. The silicone oil is provided without a cationic polymer present. A description of the suitable silicone oils is provided above as well as the level of the silicon oil that is used.

The mixture mentioned above can be provided into a wide range of products, including rinse-off products including but not limited to fabric rinse conditioners, detergents, shampoos, body washes, and other cleaning products.

A preferred embodiment of the present invention is exemplified by the following formulation:

cationic quaternary ammonia softeners from about 3 to about 30 weight percent;

polymer encapsulated capsules containing fragrance from about 0.1 to about 5 weight percent; and silicone oils from about 1 to about 10 weight percent.

The remainder of the formulation comprises water, bleaching agents, stain removers, and other ingredients known to those with skill in the art.

Further, if stability of the capsule and coating system is compromised by inclusion in the product base, product forms which separate the bulk of the base from the fragrance composition may be employed. The cationic coated polymer particles of the present invention may be provided in solid and liquid forms depending on the other materials to be used. In order to provide the cationic coated polymer in a dry form, it is preferable that the materials be dried using drying techniques well known in the art. In a preferred embodiment the materials are spray dried at the appropriate conditions. The spray dried particles may also be sized to provide for consistent particle size and particle size distribution. One application in which it would be advantageous to include dry particles of the present invention would be incorporated in a powdered laundry detergent. Alternatively wet capsule-coating slurries may be absorbed onto suitable dry powders to yield a flowable solid suitable for dry product use.

The mechanism of action of the present invention is not completely understood at this time. It is thought that the cationic polymer solution coats and associates with the polymeric capsules, thus imparting a positive charge which interacts with either the base or substrate in such a way as to substantially improve capsule deposition to the substrate surface.

It should be noted that the cationic character of the polymer coating used is not sufficient to determine whether it is functional with regard to improving capsule or particle deposition. Without wishing to be bound by theory, it is hypothesized that while cationic charge provides an affinity to the normally anionic substrates of interest (i.e., hair, skin, and cloth), other physical characteristics of the polymer are also important to functionality. Additionally, interactions between the capsule or particle surface, base ingredients, and the coating polymer are thought to be important to improving deposition to a given substrate.

Use of the coating systems described below allows for more efficient deposition of capsules, particles, and dispersed droplets that are coated by the cationically charged polymer. Without wishing to be bound by any theory it is believed that the advantages of the present invention is created by the combination of the cationically charged coating which is helpful in adhering to the substrate to which the product is applied with a capsule or particle containing fragrance. Once the encapsulated particle is adhered to the substrate we have found that the encapsulated fragrance can be delivered by the fracturing or compromising of the polymer coating by actions such as brushing hair, movement of the fabric, brushing of the skin etc.

One measurement of the enhancement of the present invention in delivering the fragrance and other ingredients of the present invention is done by headspace analysis. Headspace analysis can provide a measure of the fragrance material contained on the desired substrate provided by the present invention. The present invention will provide a much higher level of fragrance on the substrate compared to the amount of fragrance deposited on the substrate by conventional means. As demonstrated by the following examples, the present invention can deliver more than about twice the level of fragrance to a substrate than common approaches, preferably more than about three times the level of fragrance and preferably more than about five times the level of fragrance than traditional approaches.

For example, this may be determined by measuring the level of fragrance imparted to a test hair swatch containing fragrance in a shampoo by conventional means as compared to the level of fragrance imparted by the present invention. The same fragrance should be used and similar test hair pieces should be washed in a similar manner. After brushing to release the fragrance from the hair, the level of fragrance on the test hair swatches of the control and the fragrance of the present invention could be measured by headspace analysis. Due to the superior adhesion of fragrance to hair by the present invention, the headspace analysis of the respective samples will demonstrate an improved level of fragrance as compared to fragrance applied by conventional means.

To better control and measure the fragrance release upon brushing or rubbing from a substrate (i.e., hair or cotton cloth), a fixed-weight of the washed and dried substrate will be placed in a custom-made glass vessel containing SILCOSTEEL (Resteck Corp., Bellefont, Pa.) treated steel ball bearings. Headspace will be collected from the vessel using a Tenax trap (Supelco, Inc., Bellafonte, Pa.) upon equilibration. A second headspace will be collected after the substrate-containing vessel is shaken along with the steel beads on a flat bed shaker for 20 minutes. Fragrance present in the headspace from unshaken and shaken substrates and subsequently absorbed in the Tenax traps is desorbed through a Gerstel thermal desorption system (Gersteel, Inc., Baltimore, Md.). Desorbed fragrance volatiles are injected into a gas chromatograph (Hewlett-Packard, Model Agilent 6890) equipped with a flame ionization detector. Area counts of individual fragrance components, identified based on the retention time, are then collected and analyzed.

These and additional modifications and improvements of the present invention may also be apparent to those with ordinary skill in the art. The particular combinations of elements described and illustrated herein are intended only to represent only a certain embodiment of the present invention and are not intended to serve as limitations of alternative articles within the spirit and scope of the invention. All materials are reported in weight percent unless noted otherwise. As used herein all percentages are understood to be weight percent.

All U.S. patents and patent applications cited herein are incorporated by reference as if set forth in their entirety.

EXAMPLE 1

Preparation of Fragrance

The following ingredients were mixed to formulate the fragrance that was used in the following examples. Unless noted to the contrary all ingredients are available from International Flavors & Fragrances Inc., N.Y., N.Y., known to those with skill in the art as IFF.

| Ingredients | Parts by weight |
| --- | --- |
| Ethyl-2-methyl valerate | 7.143 |
| Limonene | 7.143 |
| Dihyro myrcenol | 7.143 |
| Phenyl ethyl alcohol | 7.143 |
| Benzyl acetate | 7.143 |
| Dimethyl benzyl carbonate acetate | 7.143 |
| Methyl nonyl acetaldehyde | 7.143 |
| CYCLACET (IFF) | 7.143 |
| LILIAL (Givaudan) | 7.143 |
| Hexyl salicylate | 7.143 |
| Tonalid | 7.143 |
| Geraniol | 7.143 |
| Methoxy naphthalene | 7.143 |
| Beta ionone | 7.143 |

EXAMPLE 2

Preparation of Cationic Polymer-Coated Capsules

Individual polymer solutions were prepared by mixing selected cationic polymers at 5% by weight in 50° C. warm water until fully dissolved under constant stirring. Cationic polymers used in this example are the following: cationic starch (HI-CAT CWS42 from Roquette America Inc.), cationic guar (Jaguar C-162 from Rhodia Inc.), Luviquat (HM550 and PQ11-PN from BASF Aktengesellschaft Inc.), Abil Quat (3474 from Degussa Goldschmidt Chemical Corp.), and CelQuat (L-200 from National Starch In.).

Cationic polymer-coated capsules were prepared by mixing uncoated fragrance-containing capsules and the polymer solution specified above at the level of desire. In this example, melamine-formaldehyde capsule slurry (uncoated capsules made by Cellessence International Ltd., West Molesey, Surrey, UK) that contains approximately 32% by weight of the fragrance and 57% by weight of water was used. To make the capsule slurry, a copolymer of poly acrylamide and acrylic acid was first dispersed in water together with a methylated melamine-formaldehyde resin. Fragrance was then added into the solution with high speed shearing to form small droplets. Curing of the polymeric film over the fragrance droplets as capsule wall effected by increasing the solution pH to polymerize the polymers followed by heating the solution to 50 to 85° C. To prepare cationic capsule slurry that contains cationic polymers at 63% by weight of the fragrance, 2.84 grams of the polymer solution was mixed with 0.7 grams of the capsule slurry until homogeneous.

Three different cationic capsule slurries were prepared using cationic starch (HI-CAT CWS42) at 10%, 30%, and 63% by weight of the fragrance. In the same manner, three additional cationic capsule slurries were prepared using cationic guar (Jaguar C-162) at 63%, 120%, and 300% by weight of the fragrance. Other polymers (Luviquat, Abil Quat, and Cel Quat) were used at 63% by weight of the fragrance.

EXAMPLE 3

Preparation of Control Fragrance- and Bare Capsules-Containing Shampoo for Hair Swatch Washing The control shampoo was prepared by mixing the neat fragrance at 0.75% by weight in 30 grams of model shampoo base for 5 minutes. Shampoo that contained bare capsules without a cationic coating was prepared the same way by mixing the melamine-formaldehyde capsule slurry in shampoo to obtain 0.75% by weight fragrance. The resulting fragrance- or capsules-containing shampoo was added into 570 grams of 40° C. warm water and mixed for 2 minutes. Four virgin hair swatches (approximately 2.5 grams each) were added into the warm wash liquor and shaken for another 2 minutes in a 40° C. water bath. Swatches were taken out from the wash liquor and rinsed sequentially in three glass jars that each contained 600 grams of clean warm water. Washing and rinsing were repeated once and excess water from hair was removed. Hair swatches were line-dried for 24 hours followed by sensory evaluation and analytical headspace analysis.

EXAMPLE 4

Preparation of Cationic Capsules-Containing Shampoo for Hair Swatch Washing

Cationic polymer-coated capsules prepared according to Example 2 were used to mix in 30 grams of model shampoo base to obtain a fragrance level of 0.75% by weight. The resulting shampoo was used to wash four virgin hair swatches according to the procedures described in Example 3. Hair swatches were line-dried for 24 hours followed by sensory evaluation and analytical headspace analysis.

EXAMPLE 5

Sensory Evaluation and Headspace Analysis of Hair Swatches

Dry hair swatches were evaluated by a panel of four people using the intensity scale of 0 to 5, where 0=none, 1=weak, 2=moderate, 3=strong, 4=very strong, and 5=extremely strong. Sensory scores were recorded before and after hair swatches were rubbed by hand. Deposition and release of fragrance and capsules were assessed using the purge-and-trap method followed by GC analyses on 5.0 grams of dry hair swatches before and after shaking with steel beads in enclosed vessels. Averaged sensory scores and total headspace area counts of the variables tested were reported in the following. The comment in the Table below "Encapsulated fragrance coated with cationic starch (63% fragrance)" means that the cationic starch level is 63% of the amount of fragrance.

| Hair Swatch Variable | Sensory Score (Before Rubbing) | Sensory Score (After Rubbing) |
| --- | --- | --- |
| Neat fragrance | 1.7 | 2.0 |
| Encapsulated fragrance without cationic polymer | 2.0 | 2.0 |
| Encapsulated fragrance coated with cationic starch (63% fragrance) | 3.3 | 5.0 |

| Hair Swatch Variable | Sensory Score (Before Rubbing) | Sensory Score (After Rubbing) |
|---|---|---|
| Encapsulated fragrance coated with cationic starch (30% fragrance) | 3.7 | 5.0 |
| Encapsulated fragrance coated with cationic starch (10% fragrance) | 3.0 | 4.7 |
| Encapsulated fragrance coated with cationic guar (300% fragrance) | 4.0 | 5.0 |
| Encapsulated fragrance coated with cationic guar (120% fragrance) | 2.3 | 4.7 |
| Encapsulated fragrance coated with cationic guar (63% fragrance) | 2.3 | 2.3 |
| Encapsulated fragrance coated with Luviquat HM552/PQ11-PN (63% fragrance) | 1.3 | 1.6 |
| Encapsulated fragrance coated with Abil Quat 3474 (63% fragrance) | 1.3 | 1.6 |
| Encapsulated fragrance coated with CelQuat L-200 (63% fragrance) | 1.3 | 1.3 |

|  | Neat Fragrance | | Encapsulated Fragrance Without Cationic Polymer | |
|---|---|---|---|---|
| Chemical | Unshaken | Shaken | Unshaken | Shaken |
| Ethyl-2-methyl valerate | 278 | 681 | 117 | 676 |
| Limonene | 2,081 | 4,157 | 765 | 2,527 |
| Dihydro myrcenol | 5 | 61 | 4 | 99 |
| Phenyl ethyl alcohol | 18 | 67 | 27 | 225 |
| Benzyl acetate | 16 | 71 | 13 | 55 |
| Geraniol | 0 | 0 | 0 | 0 |
| Dimethyl benzyl carbonate acetate | 9 | 181 | 5 | 88 |
| Methyl nonyl acetaldehyde | 25 | 313 | 5 | 76 |
| CYCLACET (IFF) | 10 | 139 | 74 | 66 |
| Methoxy naphthalene | 21 | 76 | 9 | 72 |
| Beta ionone | 0 | 24 | 0 | 12 |
| LILIAL (Givaudan) | 0 | 25 | 68 | 117 |
| Hexyl salicylate | 0 | 9 | 3 | 5 |
| Tonalid | 0 | 0 | 0 | 0 |
| Fragrance Total Area Count | 2,463 | 5,804 | 1,090 | 4,018 |

|  | Encapsulated Fragrance Coated with Cationic starch (63% Fragrance) | | Encapsulated Fragrance Coated with Cationic Starch (30% Fragrance) | | Encapsulated Fragrance Coated with Cationic Starch (10% Fragrance) | |
|---|---|---|---|---|---|---|
| Chemical | Unshaken | Shaken | Unshaken | Shaken | Unshaken | Shaken |
| Ethyl-2-methyl valerate | 1,253 | 27,877 | 998 | 23,570 | 1,071 | 26,914 |
| Limonene | 10,585 | 195,482 | 9,111 | 193,141 | 3,130 | 63,419 |
| Dihydro myrcenol | 292 | 20,634 | 92 | 11,864 | 198 | 12,282 |
| Phenyl ethyl alcohol | 67 | 333 | 21 | 165 | 32 | 164 |
| Benzyl acetate | 0 | 146 | 9 | 135 | 6 | 78 |
| Geraniol | 0 | 123 | 0 | 40 | 0 | 70 |
| Dimethyl benzyl carbonate acetate | 385 | 14,408 | 141 | 10,420 | 112 | 5,393 |
| Methyl nonyl acetaldehyde | 256 | 12,308 | 122 | 8,583 | 54 | 2,857 |
| CYCLACET (IFF) | 177 | 9,180 | 89 | 6,167 | 56 | 2,804 |
| Methoxy naphthalene | 41 | 831 | 21 | 492 | 20 | 506 |
| Beta ionone | 32 | 4,161 | 14 | 2,889 | 7 | 920 |
| LILIAL (Givaudan) | 27 | 2,517 | 10 | 1,743 | 4 | 509 |
| Hexyl salicylate | 9 | 412 | 3 | 304 | 0 | 63 |
| Tonalid | 0 | 33 | 0 | 27 | 0 | 7 |
| Fragrance Total Area Count | 13,124 | 288,445 | 10,631 | 259,540 | 4,690 | 115,986 |

| Chemical | Encapsulated Fragrance Coated with Cationic Guar (300% Fragrance) | | Encapsulated Fragrance Coated with Cationic Guar (120% Fragrance) | | Encapsulated Fragrance Coated with Cationic Guar (63% Fragrance) | |
|---|---|---|---|---|---|---|
| | Unshaken | Shaken | Unshaken | Shaken | Unshaken | Shaken |
| Ethyl-2-methyl valerate | 2,573 | 29,873 | 868 | 15,973 | 243 | 2,726 |
| Limonene | 11,164 | 123,014 | 5,095 | 129,185 | 1,636 | 27,218 |
| Dihydro myrcenol | 380 | 10,903 | 142 | 10,319 | 24 | 1,675 |
| Phenyl ethyl alcohol | 31 | 97 | 46 | 188 | 53 | 239 |
| Benzyl acetate | 60 | 373 | 15 | 105 | 0 | 60 |
| Geraniol | 9 | 272 | 0 | 126 | 0 | 8 |
| Dimethyl benzyl carbonate acetate | 459 | 6,874 | 113 | 7,118 | 18 | 2,959 |
| Methyl nonyl acetaldehyde | 358 | 6,760 | 82 | 5,753 | 18 | 2,108 |
| CYCLACET (IFF) | 241 | 5,011 | 57 | 4,263 | 16 | 1,209 |
| Methoxy naphthalene | 141 | 906 | 27 | 482 | 0 | 119 |
| Beta ionone | 44 | 2,459 | 12 | 2,171 | 6 | 421 |
| LILIAL (Givaudan) | 31 | 1,424 | 9 | 1,365 | 2 | 347 |
| Hexyl salicylate | 4 | 236 | 0 | 208 | 0 | 49 |
| Tonalid | 0 | 22 | 0 | 16 | 0 | 7 |
| Fragrance Total Area Count | 15,495 | 188,224 | 6,466 | 177,272 | 2,016 | 39,145 |

These results demonstrated that the following: cationic starch and cationic guar were both superior to the other cationic polymers tested, a cationic starch was far more effective than cationic guar on a same weight basis in enhancing capsule deposition on hair. Data also showed that capsule deposition was dependent on the concentration of cationic polymers present in the capsule slurry. At the highest polymer concentration of cationic starch tested (63% versus the amount of fragrance), headspace area counts suggested a total fragrance deposition was improved approximately 50-fold over the neat fragrance, i.e., non-encapsulated fragrance. Headspace area counts of cationic guar at 300% and 120% versus the amount of fragrance was found between those of cationic starch at 30% and 10% versus the amount of fragrance, although sensory scores are very close to each other which can be explained by dose-response relationship.

The averaged nitrogen to carbon ratio (by weight) of tested cationic polymers was determined as the following: 0.022, 0.0061, 0.041, 0.29, and 0.17 for Jaguar C-162, HI-CAT CWS42, Cel Quat L-200, Luviquat HM552, and Luviquat PQ11-PN, respectively. It is evident that the cationic starch used in this example did not possess the highest cationic charge density, yet best performance was obtained through the enhanced capsule deposition on hair.

EXAMPLE 6

Preparation of Control Fragrance- and Bare Capsules-Containing Powder Detergent for Fabric Swatch Washing The control powder detergent was prepared by mixing the neat fragrance prepared in Example 1 above, at 0.3% by weight in 2.13 grams of commercial powder detergent (unfragranced TIDE, Procter & Gamble). Powder detergent that contained capsules without the cationic coating was prepared the same way by mixing melamine-formaldehyde capsule slurry in detergent to obtain 0.3% by weight fragrance. The resulting fragrance- or capsules-containing detergent was added into 1-liter water in a separation glass funnel. Three terry cotton swatches (approximately 2 grams each) were added into the wash liquor and shaken for 15 minutes before the wash liquor was drained from the bottom of each funnel. Excess water was removed from swatches by syringe and swatches were rinsed with 1-liter water for additional 5 minutes using the same apparatus. Rinsing was repeated once before swatches were line-dried for 24 hours followed by sensory evaluation and analytical headspace analysis.

EXAMPLE 7

Preparation of Cationic Capsules-Containing Powder Detergent for Fabric Swatch Washing Fragrance-containing capsules with a cationic coating were prepared as described in Example 2 were used to mix in 2.13 grams of commercial powder TIDE to obtain a fragrance level of 0.3% by weight. The resulting detergent was used to wash three fabric swatches according to the procedures described in Example 6. Fabric swatches were line-dried for 24 hours followed by sensory evaluation and analytical headspace analysis.

EXAMPLE 8

Sensory Evaluation and Headspace Analysis of Fabric Swatches Washed with Powder Detergent Dry fabric swatches were evaluated by a panel of four people using the intensity scale of 0 to 5, where 0=none, 1=weak, 2=moderate, 3=strong, 4=very strong, and 5=extremely strong. Sensory scores were recorded before and after hair swatches were rubbed by hand. Deposition and release of fragrance and capsules were assessed using the purge-and-trap method followed by gas chromatography analyses on two dry fabric swatches before and after shaking with steel beads in enclosed vessels. Averaged sensory scores and total headspace area counts of the three variables tested were reported in the following:

| Fabric Swatch Variable | Sensory Score (Before Rubbing) | Sensory Score (After Rubbing) |
|---|---|---|
| Neat fragrance | 1.0 | 0.0 |
| Encapsulated fragrance without cationic polymer | 0.0 | 1.8 |
| Cationic starch-coated capsules (polymer at 100% fragrance) | 1.5 | 3.3 |

| | Neat Fragrance | | Encapsulated Fragrance Without Cationic Polymer | | Encapsulated Fragrance Coated With Cationic Starch (100% Fragrance) | |
|---|---|---|---|---|---|---|
| Chemical | Unshaken | Shaken | Unshaken | Shaken | Unshaken | Shaken |
| Ethyl-2-methyl valerate | 0 | 0 | 0 | 15 | 19 | 88 |
| Limonene | 86 | 98 | 82 | 189 | 3,343 | 57,411 |
| Dihydro myrcenol | 5 | 10 | 3 | 14 | 24 | 19 |
| Phenyl ethyl alcohol | 740 | 1,258 | 503 | 845 | 685 | 1,557 |
| Benzyl acetate | 689 | 1,991 | 207 | 669 | 298 | 1,304 |
| Geraniol | 0 | 0 | 6 | 39 | 0 | 8 |
| Dimethyl benzyl carbonate acetate | 4 | 6 | 3 | 4 | 47 | 2,224 |
| Methyl nonyl acetaldehyde | 16 | 77 | 3 | 8 | 35 | 1,542 |
| CYCLACET (IFF) | 7 | 11 | 7 | 11 | 8 | 14 |
| Methoxy naphthalene | 0 | 0 | 0 | 0 | 0 | 21 |
| Beta ionone | 0 | 0 | 2 | 0 | 0 | 357 |
| LILLIAL (Givaudan) | 0 | 10 | 4 | 8 | 4 | 235 |
| Hexyl salicylate | 0 | 11 | 3 | 7 | 4 | 9 |
| Tonalid | 0 | 0 | 0 | 0 | 0 | 14 |
| Fragrance Total Area Count | 1,547 | 3,472 | 823 | 1,809 | 4,467 | 64,803 |

"Encapsulated fragrance coated with cationic starch (100% fragrance)" means that the cationic starch level is equal to the amount of fragrance.

Sensory results showed that encapsulated fragrance materials slightly improved fragrance perception over the neat fragrance, non-encapsulated, when used with the powder detergent. This slight intensity increase, however, was not supported by the gas chromatography headspace area counts, probably due to the low overall level of components. The use of cationic starch significantly improved the fragrance deposition on cotton swatches over both bare capsules and neat fragrance. These observations were fully supported by the headspace area counts above swatches, both before and after stirred with steel beads.

EXAMPLE 9

Preparation of Control Fragrance- and Bare Capsules-Containing Fabric Softener for Fabric Swatch Washing A control was prepared by mixing the neat fragrance at 1.0% by weight in 1.0 gram of liquid fabric softener. Four different fabric softener bases were used, which were commercial Downy fragrance-free fabric softener (Procter & Gamble), model fabric softeners #1 containing 9 weight % softening surfactants, model fabric softener #2 containing 13 weight percent softening surfactant, and model fabric softener #3 containing 5 weight % softening surfactant. Fabric softener that contained capsules without cationic coating was prepared the same way by mixing the melamine-formaldehyde capsule slurry in fabric softener to obtain 1.0% by weight fragrance. The resulting fragrance- or capsules-containing softener was added into 1-liter water in a separation glass funnel. Three fabric cotton swatches (approximately 2 grams each) were added into the wash liquor and stirred for 10 minutes before the wash liquor was drained from the bottom of each funnel. Excess water was removed from swatches by syringe and swatches were line-dried for 24 hours followed by sensory evaluation and analytical headspace analysis.

EXAMPLE 10

Preparation of Cationic Capsules-Containing Fabric Softener for Fabric Swatch Washing Fragrance-containing capsules coated with cationic starch were prepared as described in Example 2 and were mixed in 1.0 gram of liquid fabric softener to obtain a fragrance level of 1.0% by weight. The resulting fabric softener was used to wash three fabric swatches according to the procedures described in Example 9. Fabric swatches were line-dried for 24 hours followed by sensory evaluation and analytical headspace analysis.

EXAMPLE 11

Sensory Evaluation and Headspace Analysis of Fabric Swatches Washed With Liquid Softener Dry fabric swatches were evaluated by a panel of four people using the intensity scale of 0 to 5, where 0=none, 1=weak, 2=moderate, 3=strong, 4=very strong, and 5=extremely strong. Sensory scores were recorded before and after fabric swatches were rubbed by hand. Deposition and release of fragrance and capsules were assessed using the purge-and-trap method followed by GC analyses on two dry fabric swatches before and after stirring with steel beads in enclosed vessels. P&G is understood to be Procter & Gamble Company of Cincinnati, Ohio. Averaged sensory scores and headspace area counts of the three variables tested were reported in the following:

| Fabric Swatch Variable | Fabric Conditioner Base | Sensory Score (Before Rubbing) | Sensory Score (After Rubbing) |
|---|---|---|---|
| Neat fragrance | P&G DOWNY ULTRA | 1.3 | 1.5 |
| Encapsulated fragrance without cationic polymer | P&G DOWNY ULTRA | 1.2 | 2.0 |
| Encapsulated fragrance coated with cationic starch (100% fragrance) | P&G DOWNY ULTRA | 1.2 | 2.2 |
| Neat fragrance | Simulated model fabric softener product base 1 | 0.9 | 1.0 |
| Encapsulated fragrance without cationic polymer | Simulated model fabric softener product base 1 | 2.3 | 3.5 |
| Encapsulated fragrance coated with cationic starch (100% fragrance) | Simulated model fabric softener product base 1 | 3.2 | 4.8 |
| Neat fragrance | Simulated model fabric softener product base 2 | 1.3 | 1.3 |
| Encapsulated fragrance without cationic polymer | Simulated model fabric softener product base 2 | 1.8 | 3.2 |
| Encapsulated fragrance coated with cationic starch (100% fragrance) | Simulated model fabric softener product base 2 | 2.2 | 3.8 |
| Neat fragrance | Simulated model fabric softener product base 3 | 1.8 | 2.3 |
| Encapsulated fragrance without cationic polymer | Simulated model fabric softener product base 3 | 1.8 | 3.0 |
| Encapsulated fragrance coated with cationic starch (100% fragrance) | Simulated model fabric softener product base 3 | 2.5 | 4.5 |

"Encapsulated fragrance coated with cationic starch (100% fragrance)" means that the cationic starch level is equal to the amount of fragrance.

| | Commercial P&G DOWNY Fabric Softener | | | | | |
|---|---|---|---|---|---|---|
| | Neat Fragrance | | Encapsulated Fragrance Without Cationic Polymer | | Encapsulated Fragrance Coated With Cationic Starch (100% Fragrance) | |
| Chemical | Unshaken | Shaken | Unshaken | Shaken | Unshaken | Shaken |
| Ethyl-2-methyl valerate | 14 | 21 | 195 | 2,038 | 452 | 2,935 |
| Limonene | 32 | 63 | 8,456 | 81,512 | 15,907 | 91,289 |
| Dihydro myrcenol | 18 | 122 | 43 | 683 | 70 | 885 |
| Phenyl ethyl alcohol | 0 | 0 | 0 | 117 | 33 | 127 |
| Benzyl acetate | 71 | 311 | 147 | 775 | 282 | 697 |
| Geraniol | 0 | 0 | 0 | 10 | 0 | 19 |
| Dimethyl benzyl carbonate acetate | 0 | 2 | 137 | 4,146 | 243 | 3,470 |
| Methyl nonyl acetaldehyde | 3 | 50 | 77 | 1,975 | 181 | 2,044 |
| CYCLACET (IFF) | 0 | 12 | 56 | 1,932 | 132 | 1,847 |
| Methoxy naphthalene | 0 | 25 | 5 | 68 | 10 | 70 |
| Beta ionone | 0 | 4 | 5 | 600 | 23 | 527 |

-continued

Commercial P&G DOWNY Fabric Softener

| Chemical | Neat Fragrance | | Encapsulated Fragrance Without Cationic Polymer | | Encapsulated Fragrance Coated With Cationic Starch (100% Fragrance) | |
|---|---|---|---|---|---|---|
| | Unshaken | Shaken | Unshaken | Shaken | Unshaken | Shaken |
| LILIAL (Givaudan) | 0 | 26 | 3 | 261 | 26 | 236 |
| Hexyl salicylate | 0 | 39 | 0 | 148 | 7 | 103 |
| Tonalid | 0 | 8 | 0 | 19 | 0 | 10 |
| Fragrance Total Area Count | 138 | 683 | 9,124 | 94,284 | 17,366 | 104,259 |

SIMULATED MODEL FABRIC SOFTENER PRODUCT BASE 1

| Chemical | Neat Fragrance | | Encapsulated Fragrance Without Cationic Polymer | | Encapsulated Fragrance Coated With Cationic Starch (100% Fragrance) | |
|---|---|---|---|---|---|---|
| | Unshaken | Shaken | Unshaken | Shaken | Unshaken | Shaken |
| Ethyl-2-methyl valerate | 0 | 0 | 552 | 8,325 | 2,354 | 27,508 |
| Limonene | 59 | 84 | 6,792 | 92,094 | 16,087 | 182,103 |
| Dihydro myrcenol | 41 | 178 | 11 | 878 | 67 | 3,764 |
| Phenyl ethyl alcohol | 0 | 0 | 0 | 0 | 0 | 141 |
| Benzyl acetate | 29 | 731 | 38 | 503 | 221 | 1,382 |
| Geraniol | 0 | 0 | 0 | 5 | 0 | 6 |
| Dimethyl benzyl carbonate acetate | 5 | 18 | 34 | 3,271 | 91 | 6,684 |
| Methyl nonyl acetaldehyde | 20 | 115 | 28 | 2,027 | 86 | 4,283 |
| CYCLACET (IFF) | 0 | 16 | 12 | 1,580 | 49 | 3,732 |
| Methoxy naphthalene | 0 | 13 | 4 | 139 | 23 | 329 |
| Beta ionone | 10 | 51 | 0 | 359 | 4 | 1,215 |
| LILIAL (Givaudan) | 0 | 28 | 0 | 208 | 3 | 617 |
| Hexyl salicylate | 0 | 42 | 0 | 65 | 0 | 216 |
| Tonalid | 0 | 10 | 0 | 10 | 0 | 22 |
| Fragrance Total Area Count | 164 | 1,286 | 7,471 | 109,464 | 18,985 | 232,002 |

SIMULATED MODEL FABRIC SOFTENER PRODUCT BASE 2

| Chemical | Neat Fragrance | | Encapsulated Fragrance Without Cationic Polymer | | Encapsulated Fragrance Coated With Cationic Starch (100% Fragrance) | |
|---|---|---|---|---|---|---|
| | Unshaken | Shaken | Unshaken | Shaken | Unshaken | Shaken |
| Ethyl-2-methyl valerate | 0 | 0 | 478 | 7,345 | 510 | 9,360 |
| Limonene | 61 | 78 | 10,762 | 151,790 | 9,775 | 177,293 |
| Dihydro myrcenol | 33 | 52 | 22 | 1,766 | 29 | 2,017 |
| Phenyl ethyl alcohol | 0 | 0 | 7 | 90 | 43 | 101 |
| Benzyl acetate | 342 | 1,696 | 208 | 2,627 | 725 | 5,019 |
| Geraniol | 0 | 3 | 0 | 13 | 0 | 15 |
| Dimethyl benzyl carbonate acetate | 4 | 12 | 29 | 5,987 | 40 | 6,347 |

SIMULATED MODEL FABRIC SOFTENER PRODUCT BASE 2 -continued

| Chemical | Neat Fragrance Unshaken | Neat Fragrance Shaken | Encapsulated Fragrance Without Cationic Polymer Unshaken | Encapsulated Fragrance Without Cationic Polymer Shaken | Encapsulated Fragrance Coated With Cationic Starch (100% Fragrance) Unshaken | Encapsulated Fragrance Coated With Cationic Starch (100% Fragrance) Shaken |
|---|---|---|---|---|---|---|
| Methyl nonyl acetaldehyde | 19 | 119 | 35 | 4,024 | 34 | 3,277 |
| CYCLACET (IFF) | 13 | 28 | 20 | 3,314 | 24 | 3,430 |
| Methoxy naphthalene | 0 | 25 | 0 | 149 | 4 | 115 |
| Beta ionone | 19 | 53 | 2 | 1,107 | 0 | 994 |
| LILIAL (Givaudan) | 51 | 454 | 0 | 608 | 0 | 425 |
| Hexyl salicylate | 0 | 75 | 0 | 263 | 0 | 200 |
| Tonalid | 0 | 21 | 0 | 37 | 0 | 21 |
| Fragrance Total Area Count | 542 | 2,612 | 11,563 | 179,120 | 11,184 | 208,614 |

SIMULATED MODEL FABRIC SOFTENER PRODUCT BASE 3

| Chemical | Neat Fragrance Unshaken | Neat Fragrance Shaken | Encapsulated Fragrance Without Cationic Polymer Unshaken | Encapsulated Fragrance Without Cationic Polymer Shaken | Encapsulated Fragrance Coated With Cationic Starch (100% Fragrance) Unshaken | Encapsulated Fragrance Coated With Cationic Starch (100% Fragrance) Shaken |
|---|---|---|---|---|---|---|
| Ethyl-2-methyl valerate | 0 | 0 | 878 | 8,607 | 1,307 | 25,601 |
| Limonene | 45 | 75 | 10,421 | 123,405 | 19,858 | 330,854 |
| Dihydro myrcenol | 15 | 41 | 118 | 1,684 | 47 | 4,431 |
| Phenyl ethyl alcohol | 0 | 0 | 0 | 218 | 9 | 249 |
| Benzyl acetate | 573 | 5,309 | 3,147 | 7,987 | 127 | 1,070 |
| Geraniol | 0 | 0 | 0 | 22 | 0 | 27 |
| Dimethyl benzyl carbonate acetate | 0 | 9 | 217 | 4,854 | 102 | 10,430 |
| Methyl nonyl acetaldehyde | 6 | 124 | 173 | 2,951 | 105 | 7,410 |
| CYCLACET (IFF) | 0 | 12 | 122 | 2,599 | 52 | 6,724 |
| Methoxy naphthalene | 0 | 8 | 13 | 119 | 7 | 304 |
| Beta ionone | 0 | 4 | 16 | 886 | 4 | 2,301 |
| LILIAL (Givaudan) | 0 | 34 | 10 | 456 | 3 | 1,215 |
| Hexyl salicylate | 0 | 44 | 0 | 191 | 0 | 518 |
| Tonalid | 0 | 13 | 0 | 24 | 0 | 68 |
| Fragrance Total Area Count | 639 | 5,673 | 15,115 | 154,003 | 21,621 | 391,202 |

Sensory data indicated that cationic starch improved capsule deposition in all tested rinse conditioners. The specific base composition is a factor that influences deposition and the magnitude of perceived sensory. Analytical headspace area counts confirmed this observation.

What is claimed is:

1. A composition comprising: a fragrance material; said fragrance material encapsulated by a polymer selected from the group consisting of a blend of an acrylate polymer and melamine-formaldehyde to provide a polymer encapsulated fragrance; the polymer encapsulated fragrance is further coated by a cationic polymer selected from the group cationically modified starch, cationically modified guar, and mixtures thereof; and wherein the fragrance is a liquid thereby providing a liquid core to the polymer encapsulated fragrance.

2. The composition of claim 1 wherein the fragrance material is not water soluble.

3. The composition of claim 1 wherein the fragrance material is from about 10 to about 50 weight percent of the composition.

4. The composition of claim 1 which is incorporated into a product selected from the group consisting of a personal care, fabric care and cleaning products.

5. The composition of claim 4 wherein the personal care product is selected from the group consisting of hair shampoos, hair rinses, bar soaps, and body washes.

6. A method for imparting an olfactory effective amount of fragrance into a wash-off product comprising:
providing a fragrance material;
encapsulating the fragrance material with a polymer selected from the group consisting of a blend of an acrylate polymer and melamine-formaldehyde to form a polymer encapsulated fragrance; providing a cationic polymer selected from the group consisting of cationically modified starch and cationically modified guar and coating the surface of the polymer encapsulated fragrance therewith to form a cationically coated polymer encapsulated material; and providing the cationically coated polymer encapsulated material to a rinse off product.

* * * * *